United States Patent
Moon

(10) Patent No.: US 7,479,009 B2
(45) Date of Patent: Jan. 20, 2009

(54) ORTHODONTIC BRACKET BASE AND BRACKET USING THE BASE

(76) Inventor: Seung Soo Moon, 325-31, Daeheung-dong, Mapo-gu, Seoul (KR) 121-810

( * ) Notice: Subject to any disclaimer, the term of this patent is extended or adjusted under 35 U.S.C. 154(b) by 0 days.

(21) Appl. No.: 11/436,368

(22) Filed: May 18, 2006

(65) Prior Publication Data

US 2006/0263736 A1      Nov. 23, 2006

(30) Foreign Application Priority Data

May 20, 2005   (KR)   .................. 10-2005-0042657

(51) Int. Cl.
     *A61C 3/00*       (2006.01)
(52) U.S. Cl. .................. 433/9; 433/10; 433/11
(58) Field of Classification Search ............ 433/8–11, 433/13
     See application file for complete search history.

(56) References Cited

U.S. PATENT DOCUMENTS 4,919,615 A * 4/1990 Croll ........................ 433/3
2003/0190577 A1* 10/2003 Shin et al. .................. 433/9
2004/0219470 A1* 11/2004 Farzin-Nia .................. 433/3

FOREIGN PATENT DOCUMENTS

| JP | 2004-329936 | 11/2004 |
| KR | 20-0378039 | 3/2005 |

* cited by examiner

*Primary Examiner*—John J Wilson
*Assistant Examiner*—Heidi M Bashaw
(74) *Attorney, Agent, or Firm*—The Webb Law Firm

(57) ABSTRACT

Disclosed is an orthodontic bracket which has excellent adhesion to a tooth surface and can be easily separated from the tooth surface after orthodontic treatment is finished. The base of the orthodontic bracket comprises an adhesion surface brought into dose contact with a tooth surface; a central projection located at a center portion of the adhesion surface; and a plurality of surrounding projections arranged at regular intervals around the central projection and made of a material which allows force of adhesion to the tooth surface of an adhesive to be greater at the surrounding projections than at the central projection.

4 Claims, 4 Drawing Sheets

[FIG. 1] - PRIOR ART
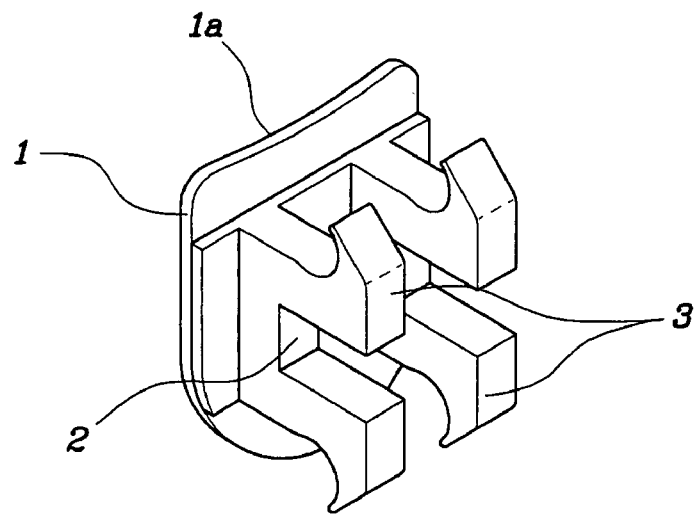
[FIG. 2] - PRIOR ART
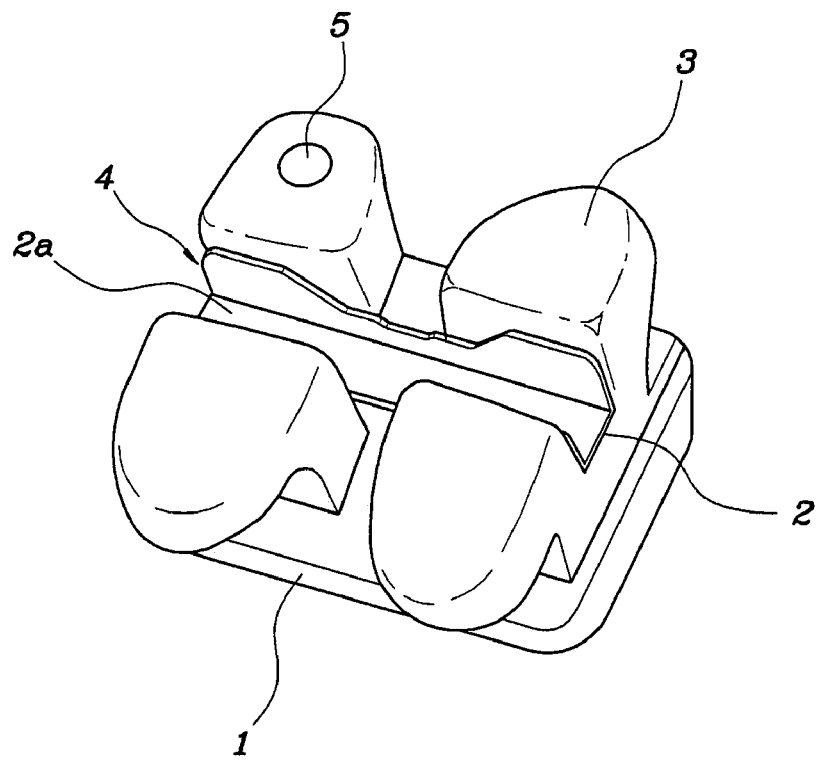

[FIG. 3]
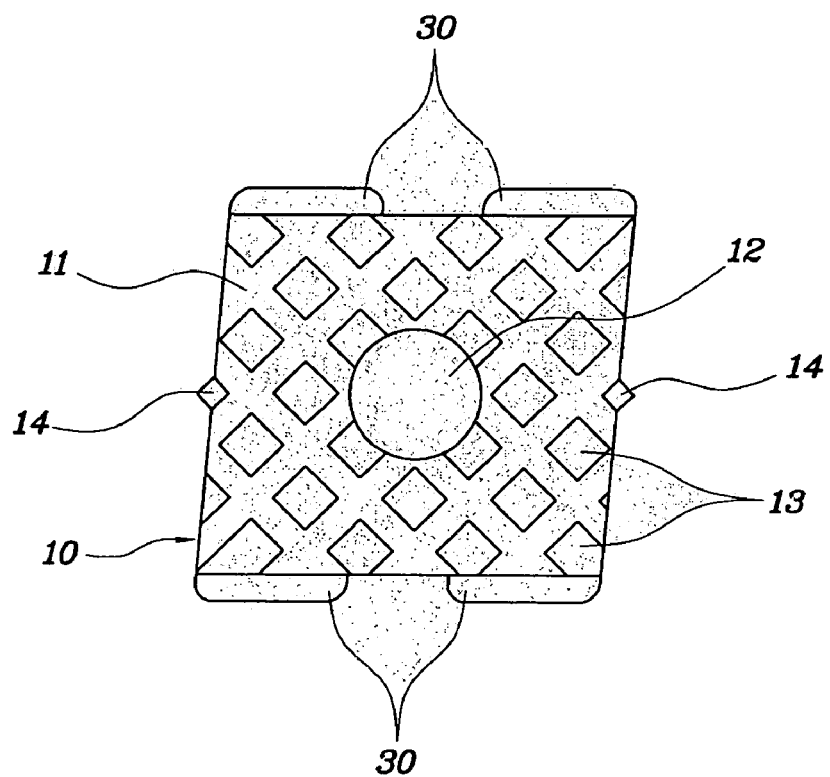
[FIG. 4]
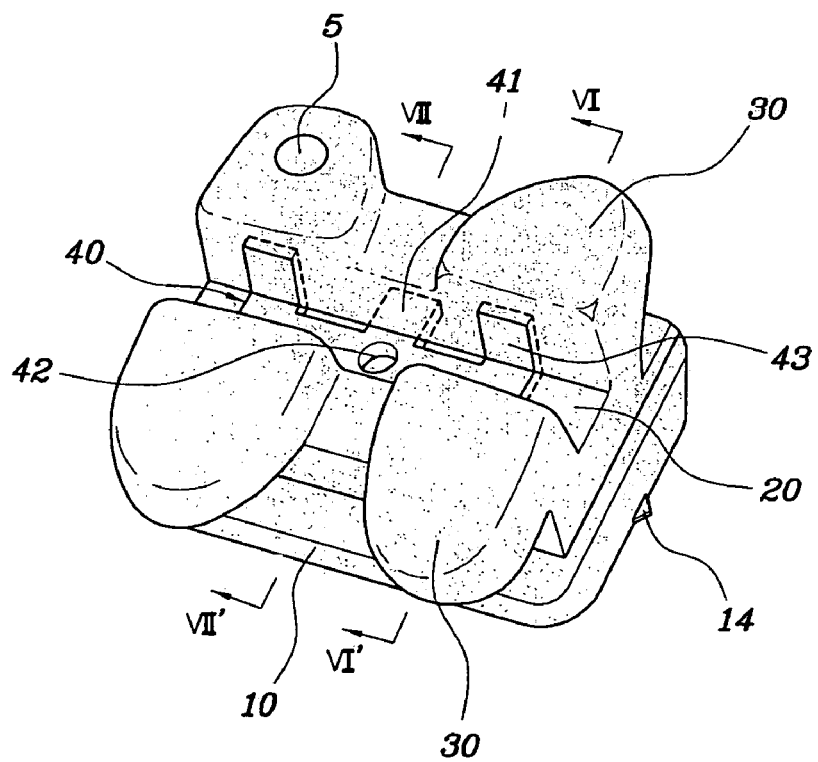

[FIG 5]
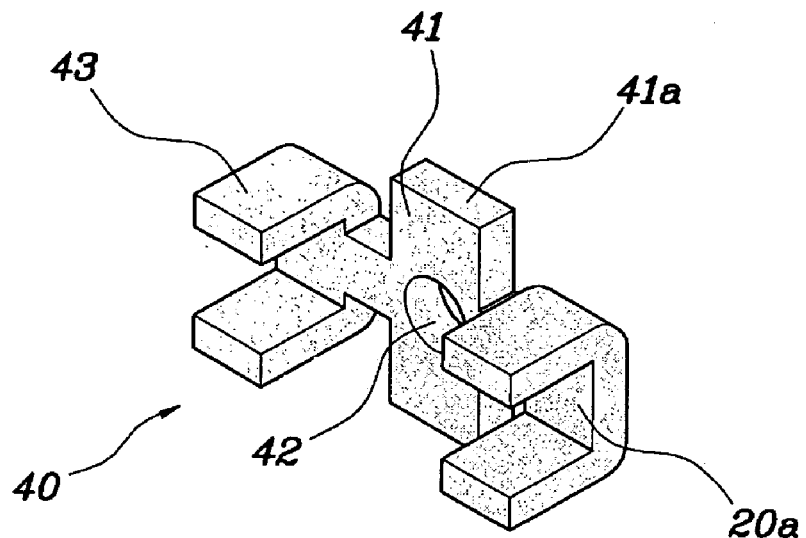
[FIG. 6]
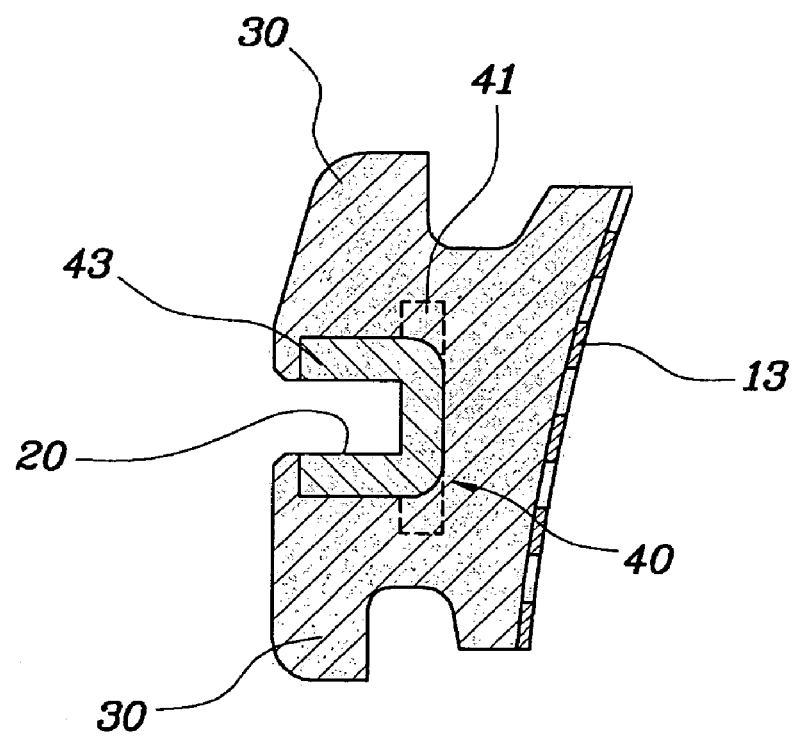

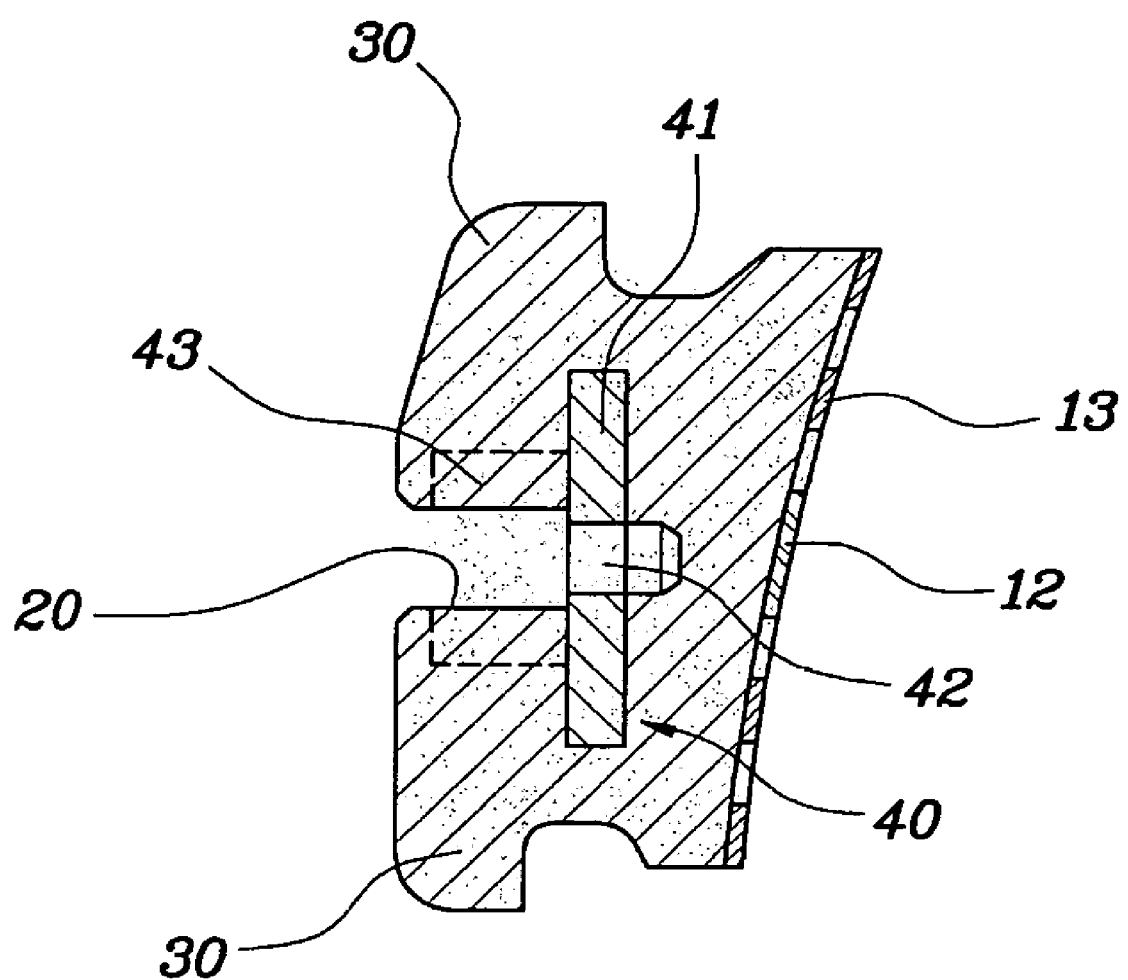
[FIG. 7]

ORTHODONTIC BRACKET BASE AND BRACKET USING THE BASE

BACKGROUND OF THE INVENTION

1. Field of the Invention

The present invention relates, in general, to an orthodontic bracket base and an orthodontic bracket having the base, and more particularly, to an orthodontic bracket base which has a characteristic of excellent adhesion to a tooth surface and can be easily separated from the tooth surface after orthodontic treatment is finished, and to an orthodontic bracket having the base.

2. Description of the Prior Art

As is generally known in the art, the parts used for correcting an irregularly arranged set of teeth mostly include orthodontic brackets (hereinafter, referred to as "brackets"), each of which is secured to a tooth surface, and an arch wire which connects the brackets to one another so as to apply tension force to thereby correct the irregular set of teeth.

Referring to FIG. 1, a metal bracket is illustrated as one example of a conventional bracket. As can be seen from FIG. 1, the bracket comprises a base 1 which has an adhesion surface 1a to be brought into dose contact with a tooth surface, a slot 2 which is defined on the rear surface of the base 1 to allow a wire (not shown) to be fitted therein, and wings 3 which are arranged on both sides of the slot 2 to allow a securing member for securing the wire, such as an elastic O-ring, a bolt, and so forth, to be mounted thereto.

Basically, the bracket must not be easily separated from the tooth surface while orthodontic treatment is underway (hereinafter, referred to as an "adhesion function"), and must be easily separated from the tooth surface after orthodontic treatment is finished (hereinafter, referred to as a "separation function").

As a method for improving the adhesive function of the bracket, that is, for allowing the adhesion surface of the base to be adhered to the tooth surface with a sufficient adhesive strength, a first method of improving the functionality of an adhesive, a second method of changing the contour of the adhesion surface such as by forming prominences and depressions or slits or grooves on the adhesion surface of the base, a third method of using mesh prepared by weaving thin wire, etc. are currently known in the art.

For example, in Korean Utility Model Registration No. 20-378093, in order to improve the adhesion strength of a bracket, prominences and depressions are formed on an adhesion surface, and mesh is heat-fused onto the prominences and depressions.

However, in this conventional technique, special emphasis is placed only on improving the adhesive function, and the importance of the separation function is not appropriately considered. Therefore, a problem occurs in that it is difficult to separate the bracket from the tooth surface to the extent that the adhesion strength of the bracket with respect to the tooth surface is improved. Further, serious damage to the tooth surface may occur.

In Japanese Patent Laid-open Publication Gazette 2004-329936, in order to improve the separation function of the bracket, disclosed is a technique of making the adhesive force smaller adjacent to the edges of the adhesion surface of a base compared to other portions.

Nevertheless, in this conventional technique, special emphasis is placed only on the improvement of the separability of the bracket, and measures for solving the problem caused by the degradation of the adhesive function which results from the improvement of the separation function are not provided.

Meanwhile, FIG. 2 illustrates another example of the conventional bracket, which is a metal-reinforced ceramic bracket. Since the ceramic bracket is transparent and has an aesthetically appealing outer appearance, it is preferable to a metal bracket.

Referring to FIG. 2, the bracket comprises a base 1, a slot 2 and wings 3. The base 1 and the wings 3 are mainly made of ceramic. A metal insert 4 for reinforcing the strength of the bracket is installed in the slot 2. The insert 4 also has a slot 2a which corresponds to the slot 2. The unexplained reference numeral 5 designates a dimple portion on which a bracket identification marking is provided.

Even in the type of bracket shown in FIG. 2, a drawback exists in that the insert 4 is likely to be released from its normal installation position due to the movement of a wire fitted into the slot 2a of the insert 4 in the course of performing ligation.

SUMMARY OF THE INVENTION

Accordingly, the present invention has been made keeping in mind the above problems occurring in the prior art, and an object of the present invention is to provide an orthodontic bracket base which has an appropriately balanced adhesive function and separability, and an orthodontic bracket having the base.

Another object of the present invention is to provide an orthodontic bracket which is constructed to prevent an insert from being released from a slot.

In order to achieve the above objects, according to one aspect of the present invention, there is provided an orthodontic bracket base comprising an adhesion surface brought into close contact with a tooth surface; a central projection located at a center portion of the adhesion surface; and a plurality of surrounding projections arranged at regular intervals around the central projection and made of a material which causes force of adhesion to the tooth surface due to an adhesive to be greater at the surrounding projections than at the central projection.

Thanks to the features of the bracket base, an excellent characteristic of adhesion of the bracket to the tooth surface is obtained, and the bracket can be easily separated from the tooth surface after orthodontic treatment is finished.

The bracket base can be applied to all kinds of orthodontic brackets such as a metal bracket, a metal-reinforced ceramic bracket, a ceramic bracket not comprising a metal insert, a resin bracket, and the like. The adhesive can include all products which are conventionally used to secure an orthodontic bracket to a tooth surface.

According to another aspect of the present invention, provided is an orthodontic bracket comprising a base having an adhesion surface brought into dose contact with a tooth surface, a central projection located at a center portion of the adhesion surface, and a plurality of surrounding projections arranged at regular intervals around the central projection and made of a material which causes adhesive force from an adhesive to be greater at the surrounding projections than at the central projection; a slot defined on the rear surface of the base to allow a wire to be fitted therein; wings located on both sides of the slot to allow securing members for securing the wire to be installed on them; and an insert installed in the slot to reinforce the strength of the orthodontic bracket, the insert having an insert body which has a cross-shaped configuration to prevent the insert from being moved in the lengthwise direction of the slot and arm portions which are bent from the side edges of the insert body to define a U-shaped section.

Thanks to the features of the bracket, in addition to the above-mentioned working effects obtained due to the construction of the bracket base, the insert can be prevented from being released from the slot.

BRIEF DESCRIPTION OF THE DRAWINGS

The above and other objects, features and other advantages of the present invention will be more clearly understood from the following detailed description when taken in conjunction with the accompanying drawings, in which:

FIG. 1 is a perspective view illustrating one example of a conventional orthodontic bracket;

FIG. 2 is a perspective view illustrating another example of a conventional orthodontic bracket;

FIG. 3 is a front view illustrating an orthodontic bracket in accordance with an embodiment of the present invention;

FIG. 4 is a rear perspective view of the orthodontic bracket shown in FIG. 3;

FIG. 5 is a perspective view independently illustrating an insert installed in the orthodontic bracket shown in FIG. 3;

FIG. 6 is a cross-sectional view taken along the line VI-VI' of FIG. 5; and

FIG. 7 is a cross-sectional view taken along the line VII-VII' of FIG. 5.

DETAILED DESCRIPTION OF THE INVENTION

Reference will now be made in greater detail to a preferred embodiment of the invention, an example of which is illustrated in the accompanying drawings. Wherever possible, the same reference numerals will be used throughout the drawings and the description to refer to the same or like parts.

Referring to FIGS. 3 through 7, a metal-reinforced ceramic bracket is illustrated as an example of a bracket according to the present invention.

As shown in FIGS. 3 and 4, the bracket comprises a base 10 secured to a tooth surface, a slot 20 defined on the rear surface of the base 10 to allow a wire (not shown) to be fitted therein, wings 30 arranged at both sides of the slot 20, and an insert 40 installed in the slot 20.

The base 10 is a member which has a predetermined thickness and a substantially rectangular configuration. The front surface of the base 10 is directly bonded to the tooth surface using an adhesive. On the rear surface of the base 10 are provided members for installation of the wire. In this description, the front surface of the base 10 is specifically referred to as an adhesion surface 11.

The adhesion surface 11 has the same surface contour as the tooth surface so that it can be brought into dose contact with the tooth surface (see FIGS. 7 and 8). On the adhesion surface 11 are formed one central projection 12 and a plurality of surrounding projections 13 which project to 0.2~0.3 mm. If the projection height of the central projection 12 and the surrounding projections 13 is less than 0.2 mm, the projections 12 and 13 cannot properly perform their functions. If the projection height of the central projection 12 and the surrounding projections 13 is greater than 0.3 mm, since the thickness of the bracket is increased, when the bracket is installed on the tooth surface of a patient, the patient can feel the sensation of a foreign object.

The central projection 12 has a circular column-shaped configuration. The central projection 12 is located at the center of the adhesion surface 11 and has a diameter of 1.0~1.5 mm.

Preferably, the central projection 12 is formed of stainless steel so that the adhesion surface 11 attached to the tooth surface using the adhesive can be easily separated from the tooth surface after the orthodontic treatment is finished. Of course, the central projection 12 may be formed of another material, specifically, a metal alloy which has the same force of adhesion to the tooth surface as the stainless steel when the material is bonded to the tooth surface using the adhesive.

The surrounding projections 13 have a square column-shaped configuration. The surrounding projections 13 are arranged around the central projection 12 at regular intervals. Specifically, the surrounding projections 13 are arranged in a diagonal direction on the adhesion surface 11. The facing sides of the surrounding projections 13 which adjoin one another in diagonal directions are parallel to one another.

Some of the surrounding projections 13 which are adjacent to the edges of the base 10 extend to the edges of the adhesion surface 11. Due to this fact, a minimum of a predetermined level of adhesion force can be maintained between the tooth surface and the edges of the adhesion surface 11.

The surrounding projections 13 are formed of resin, ceramic or a mixture thereof which allows force of adhesion to the tooth surface due to the adhesive to be greater at the surrounding projections 13 than at the central projection 12. Preferably, each of the surrounding projections 13 has a smaller area of contact with the tooth surface than the central projection 12.

According to the structure of the adhesion surface 11 as described above, since the surrounding projections 13 having good force of adhesion to the adhesive are evenly distributed over the entire adhesion surface 11, excellent adhesion can be accomplished between the adhesion surface 11 and the tooth surface. Moreover, since the force to be transmitted to the bracket through the wire, etc. can be evenly dispersed over the entire adhesion surface 11, the state of adhesion between the adhesion surface 11 and the tooth surface can be stably maintained.

Meanwhile, due to the fact that the central projection 12, which has adhesion force less than that of the surrounding projections 13, is located at the center of the adhesion surface 11, the adhesion surface 11 can be separated from the tooth surface relatively easily. Further, the peculiar configuration and the location of the surrounding projections 13 at the edges of the adhesion surface 11 not only increases the force of adhesion between the edges of the adhesion surface 11 and the tooth surface, but also ensures easy separation of the bracket from the tooth surface.

The adhesion surface 11 has a pair of separation elements 14 to be grasped using pliers, etc., used for separating the bracket from the tooth surface.

The separation elements 14 are formed opposite each other on the edges of the adhesion surface 11 and project from the adhesion surface 11. Preferably, the width of each separation element 14 gradually decreases as the separation element 14 extends away from the base 10 so that the separation element 14 which extends outside the edge of the adhesion surface 11 has a triangular shape. The projection height of the separation element 14 toward the front surface of the base 10 may be smaller than that of the central and surrounding projections 12 and 13.

The structure of the rear surface of the bracket base 10 will be described below with reference to FIGS. 4 through 7.

The slot 20 is defined in the shape of a channel which extends across the rear surface of the base 10. The slot 20 has predetermined width and depth so that the wire (not shown) can be fitted therein.

The wings 30 serve as members on which securing members for securing the wire, such as an elastic O-ring, a bolt, and so forth, are installed. Two pairs of wings 30 are located on both sides, respectively, of the slot 20. The unexplained reference numeral 5 designates a dimple portion.

An insert 40 made of a metallic material is installed in the slot 20 to reinforce the strength of the bottom surface of the slot 20 which is brought into contact with the wire.

The insert 40 comprises an insert body 41 which has a cross-shaped configuration and arm portions 43 which are bent from both side edges of the insert body 41 to define a U-shaped section. In particular, both vertical ends 41a of the cross-shaped insert body 41 are inserted into and secured to the base 10 at both sides of the slot 20. Due to this fact, the problem of the conventional insert, which is that it can be released in the lengthwise direction of the slot 20, can be solved.

The wire fitted into the insert 40 can be supported by a metal slot part 20a and the arm portions 43. A bolt hole 42, into which a bolt (not shown) for securing the wire or adjusting the tension of the wire is inserted, is defined in the center portion of the insert body 41. A hole, which communicates with the bolt hole 42 of the insert 40, can be defined in the bottom surface of the slot 20.

The metal insert 40 is incorporated in the ceramic body having the base 10 and wings 30, through insert molding in the process of forming the ceramic body from ceramic material.

Otherwise, the metal insert can be coupled to the ceramic material by being press-fitted into the slot of the ceramic material. In this case, both vertical ends of the cross-shaped insert body can be fitted into the space defined between the wings (see FIG. 2).

When attaching the bracket, constructed as mentioned above, to the tooth surface, it is necessary to evenly apply the adhesive over the entire adhesion surface 11 of the base 10. At this time, it is preferred that, when the adhesive is applied to the central projection 12, the surrounding projections 13 and the adhesion surface 11 between the projections 12 and 13, the surface of the applied adhesive be maintained at a consistent level. By doing so, the adhesion surface 11 applied with the adhesive can be brought into contact with the tooth surface and be firmly secured to the tooth surface.

When separating the bracket from the tooth surface after orthodontic treatment is finished, the separation elements 14 formed on the edges of the adhesion surface 11 are grasped using pliers, etc., and force is slowly applied to the bracket in a leftward or rightward direction. Due to this force, the central projection 12, which has the smallest adhesive force, is separated from the tooth surface first. Thereafter, as the gap created between the central projection 12 and the tooth surface is gradually propagated around the central projection 12, the bracket can be easily separated from the tooth surface.

As is apparent from the above description, the orthodontic bracket base and the orthodontic bracket having the base according to the present invention provide advantages in that an excellent characteristic of adhesion of the bracket to a tooth surface is obtained, and the bracket can be easily separated from the tooth surface after orthodontic treatment is finished.

Also, the insert is prevented from being released from the slot.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An orthodontic bracket base comprising:
   an adhesion surface, having edges, to be brought into close contact with a tooth surface;
   a central projection having a circular column-shaped configuration with a diameter of 1.0~1.5 mm and height of 0.2~0.3 mm, being located at a center portion of the adhesion surface, and being made of stainless steel or other material having the same force of adhesion as stainless steel;
   a plurality of surrounding projections, each of which having a square column-shaped configuration with a height of 0.2~0.3 mm and having a smaller area of contact with the tooth surface than the central projection, being arranged in diagonal directions with regular intervals around the central projection, and being made of resin, ceramic or mixture thereof; and
   a pair of separation elements oppositely formed on the edges of the adhesion surface and project outside the adhesion surface, each of which having a smaller area of contact with the tooth surface than any of the surrounding projections, and having a width that gradually decreases as it extends away from the edge of the adhesion surface.

2. The orthodontic bracket base according to claim 1, wherein facing sides of the surrounding projections which adjoin one another in the diagonal directions are parallel to one another.

3. The orthodontic bracket base according to claim 2, wherein the surrounding projections which are adjacent to edges of the adhesion surface extend to the edges of the adhesion surface.

4. An orthodontic bracket comprising:
   a base comprising:
      an adhesion surface, having edges, to be brought into close contact with a tooth surface;
      a central projection having a circular column-shaped configuration with a diameter of 1.0~1.5 mm and height of 0.2~0.3 mm, being located at a center portion of the adhesion surface, and being made of stainless steel or other material having the same force of adhesion as stainless steel;
      a plurality of surrounding projections, each of which having a square column-shaped configuration with a height of 0.2~0.3 mm and having a smaller area of contact with the tooth surface than the central projection, being arranged in diagonal directions with regular intervals around the central projection, and being made of resin, ceramic or mixture thereof; and
   a pair of separation elements oppositely formed on the edges of the adhesion surface and project outside the adhesion surface, each of which having a smaller area of contact with the tooth surface than any of the surrounding projections, and having a width that gradually decreases as it extends away from the edge of the adhesion surface;
   a slot defined as a cross-shaped groove on a rear surface of the base;
      two pairs of wings, each being located on each side of the slot; and an insert having an insert body including a cross-shaped configuration to be fitted into the cross-shaped groove of the slot, and two U-shaped arm portions each formed at terminal of the insert body.

* * * * *